United States Patent [19]
Bondi et al.

[11] Patent Number: 4,942,037
[45] Date of Patent: Jul. 17, 1990

[54] TRANSDERMAL DELIVERY SYSTEMS

[75] Inventors: Joseph V. Bondi, Collegeville; Alice E. Loper, Lederach, both of Pa.

[73] Assignee: Merck & Co., Inc., Rahway, N.J.

[21] Appl. No.: 202,088

[22] Filed: Jun. 2, 1988

[51] Int. Cl.$^5$ .............................................. A61F 13/02
[52] U.S. Cl. ................................... 424/448; 424/447; 424/449
[58] Field of Search ................................ 424/449, 448

[56] References Cited

U.S. PATENT DOCUMENTS

| | | | |
|---|---|---|---|
| 3,598,122 | 8/1971 | Zaffaroni | 424/448 |
| 4,336,243 | 6/1982 | Sanvordeker et al. | 424/449 |
| 4,420,480 | 12/1983 | Jones | 514/229.8 |
| 4,797,284 | 1/1989 | Loper et al. | 429/448 |

FOREIGN PATENT DOCUMENTS 1361289 7/1974 United Kingdom .

OTHER PUBLICATIONS

W. Koller et al., Movement Disorders, vol. 1, No. 190, 1987, pp. 193-199.
Carelli, V. et al., Int. J. Pharmaceutics, 35, 21-28 (1987).
Chien, Y. W., Pharm. Technology 9(5), 50-66 (1985).
Hsieh, D. S. T. et al., Drug Devel. Ind. Pharm., 11(6 & 7), 1391-1410 (1985) (I).
Hsieh, D. T. S. et al., Drug Devel. Ind. Pharm., 11(6 & 7), 1411-1432 (1985) (II).
Martin, G. E. et al., J. Pharm. & Exptl. Thera. 230 (3), 569-576 (1984).
Ritschel, W. A. et al., Arzneim.-Forsch. Drug Res. 37(I), 302-306 (1987).
Robertson, D. N., "Implantable Levonorgestrel Rod Systems: In Vivo Release Rates and Clinical Effects", Proc. Intl. Workshop, Long-Acting Contraceptive Delivery Systems, May 31-June 3, 1983, New Orleans, La., Harper & Row, Philadelphia.

Primary Examiner—Thurman K. Pace
Assistant Examiner—Leon R. Horne
Attorney, Agent, or Firm—Alice O. Robertson; Joseph F. DiPrima

[57] ABSTRACT

A transdermal delivery system suitable for the drug (4aR-trans)- 3, 4, 4a, 5, 6, 10b-hexahydro-4-propyl-2H-naphth[1,2-b]-1,4-oxazin-9-ol over an extended period of time is described.

2 Claims, 3 Drawing Sheets

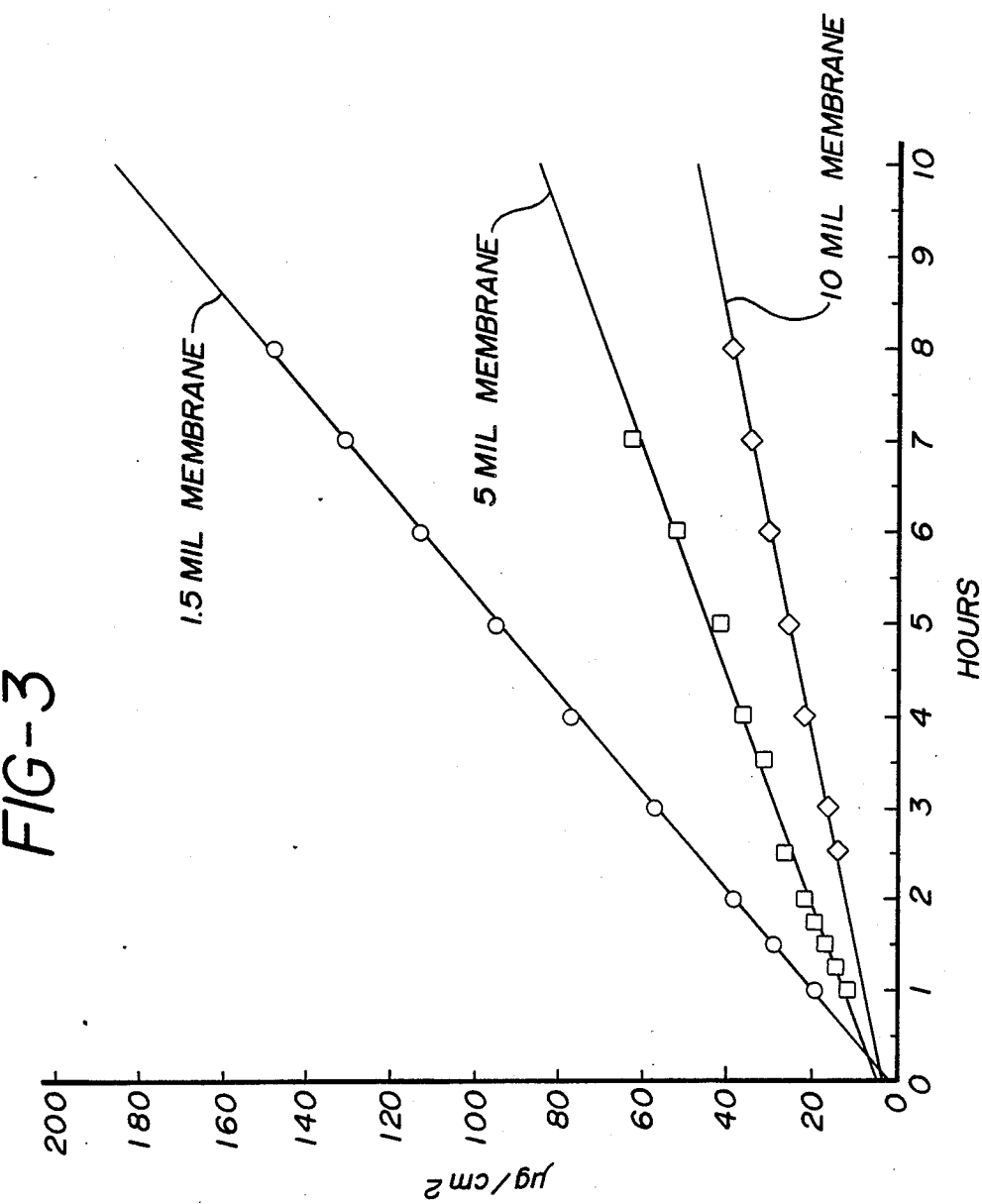

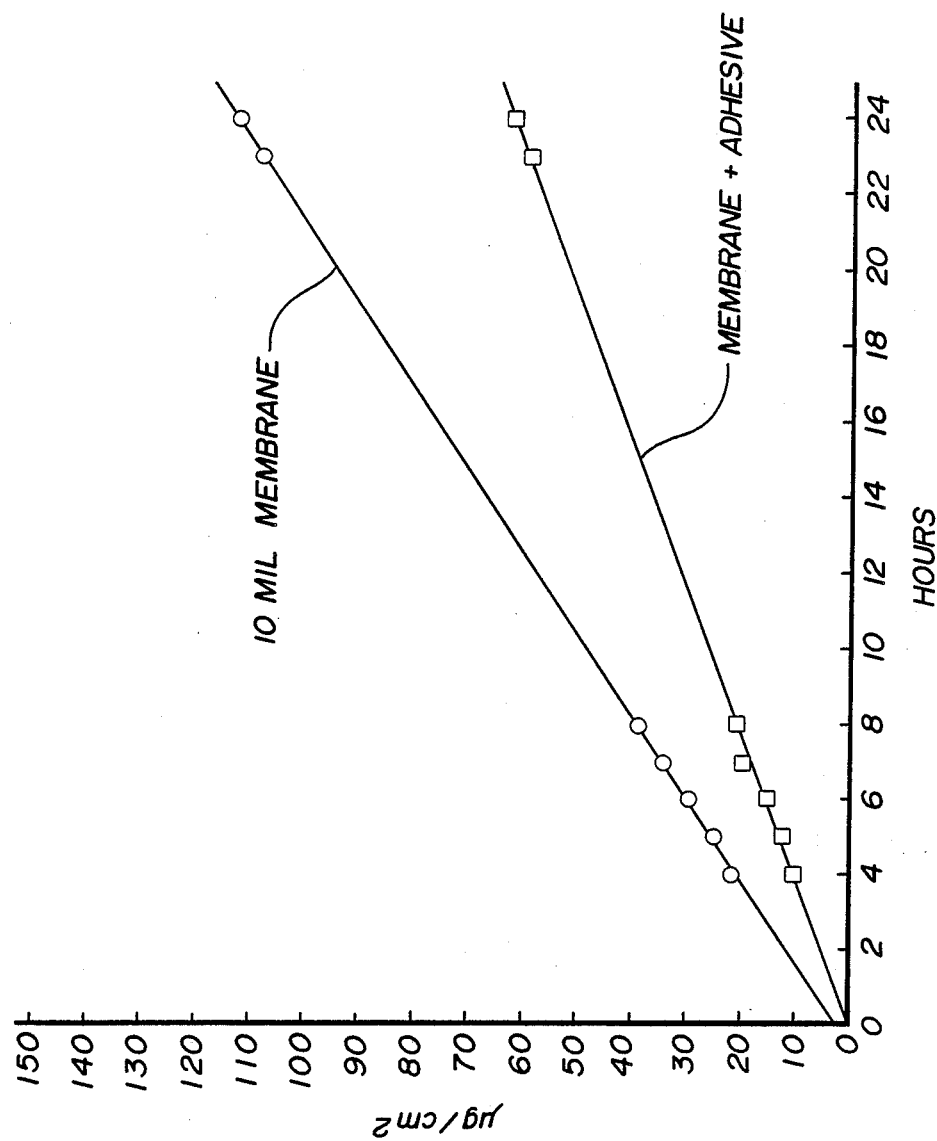

TRANSDERMAL DELIVERY SYSTEMS

The present invention is concerned with a transdermal delivery system suitable for the administration of (4aR-trans)-3,4,4a,5,6,10b-hexahydro-4-propyl-2H-naphth[1,2-b]1,4-oxazin-9-ol over an extended period of time.

BACKGROUND OF THE INVENTION (4aR trans) 3,4,4a,5,6,10b hexahydro 4-propyl-2H-naphth[1,2-b]-1,4-oxazin-9-ol (Compound I) represented by the formula

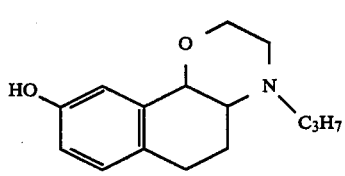

is a highly potent dopamine agonist and is useful in the treatment of Parkinson's disease. The compound was first called (+)-4-propyl-9-hydroxynaphthoxazine and is often referred to by that name or by (+)-PHNO in the pharmacological and clinical literature. It is also known in the literature as trans-1a,2,3,-4a,5,6-hexahydro-9-hydroxy-4-propyl-4H-naphth[1,2]-1,4-oxazine. For convenience, it will hereinafter be referred to generally by (+)-PHNO. The compound is a white powder with a melting point of 162°–164° C. as a free base and 300° C. as the hydrochloride salt. The preparation of the drug is described in U.S. Pat. No. 4,420,480. The pharmacological properties may be found described in an article by G. E. gartin et al., J. Pharm. & Exptl Ther. 230 569(1984).

Treatment entails long term therapy. It has been found that erratic durations of action develop and managing fluctuations is the most troublesome issue in oral treatment of Parkinson's disease either with levodopa or dopamine agonists. One of the ways which may be employed to overcome the problem of fluctuation is to employ intravenous infusion. However, this is a burdensome method.

Oral administration of (+)-PHNO at desirable doses may produce vomiting and other side reactions. Another method of application of the drug attempted was application to the skin using a hydroalcoholic solution. However, the solution dried to a viscous residue and provided uncontrolled delivery of the drug to the skin. Safe handling of this solution by the patient was not possible.

Thus, it is desirable to provide a safe and effective means for administering (+)-PHNO over an extended period at a suitably and reliably controlled rate.

STATEMENT OF THE INVENTION

According to the present invention it has been discovered that the desired therapeutic dose of (4aR-trans)-3,4,4a,5,6,10b-hexahydro-4-propyl-2H-naphth[1,2-b]-1,4-oxazin-9-ol ((+)-PHNO) may be provided at a constant rate over a prolonged period of time by administering the drug in a transdermal delivery system in which the drug is released from a solid reservoir matrix of cured silicone polymer containing glycerol.

DESCRIPTION OF THE INVENTION

The transdermal delivery system of the present invention comprises a solid state drug reservoir of biologically acceptable cross-linked silicone rubber polymer matrix affixed to a backing and containing therein (+)-PHNO in excess of its solubility together with glycerol as a cosolvent and faced with a rate-controlling membrane.

By "solid state" matrix is meant one that does not exhibit significant flow properties.

It is essential that the matrix be of a silicone rubber polymer. Silicone rubber polymers are dimethylpolysiloxanes which may have some of the methyl groups substituted with phenyl groups or vinyl groups to achieve variation in properties and which may be cured or vulcanized either at room temperature or at elevated temperatures. Preparation and properties of these polymers are described in standard references and the polymers are available commercially. Suitable silicone polymers are those which permit curing to proceed in the presence of drug and at the same time does not adversely affect the drug.

A still further essential component of the solid state silicone reservoir is glycerol. The partitioning effect of the matrix silicone and glycerol cosolvent on (+)-PHNO facilitates the delivery of the drug.

Thus, a particular aspect of the present invention is a novel reservoir composition which permits a safe and efficient method for administering (+)-PHNO. The novel reservoir composition comprises (+)-PHNO and glycerol in a silicone rubber. The amount of (+)-PHNO is from about 1 to about 5 percent by weight The amount of glycerol may be from about 0.5 to no greater than about 40 percent.

The rate-controlling membrane is also of silicone elastomer. The membrane is of a similar polymer but of greater hardness and offering greater resistance to penetration and dissolution of the drug.

In addition, the membrane in turn may be faced with an adhesive, said adhesive facing being suitable for affixing the transdermal delivery system containing (+)-PHNO to the skin thereby providing a patch or bandage. Generally, the facing adhesive also has some rate-controlling properties so that the actual rate of delivery will be the combined effects of flux through the reservoir and the membrane and adhesive layers.

The transdermal delivery system and the transdermal patch may best be seen with reference to the drawings.

Figure 1:
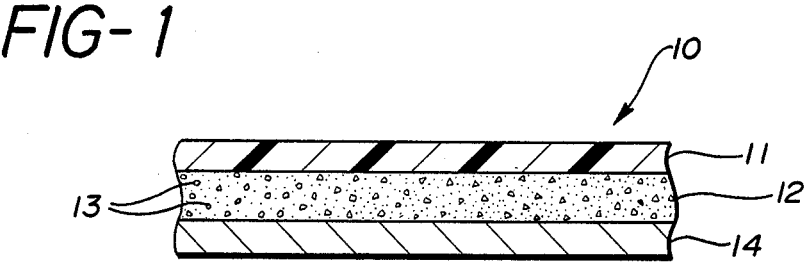
FIG. 1 is a fragmentary enlarged cross-sectional view depicting the essential component elements of a transdermal delivery system for (+)-PHNO.

Referring to the drawings, there is shown in FIG. 1, a transdermal delivery system 10 which comprises an impermeable backing member 11, a drug reservoir member 12 comprising a continuous matrix containing dissolved drug and cosolvent, with undissolved drug 13 dispersed therein, and a rate controlling membrane member 14.

Figure 2:
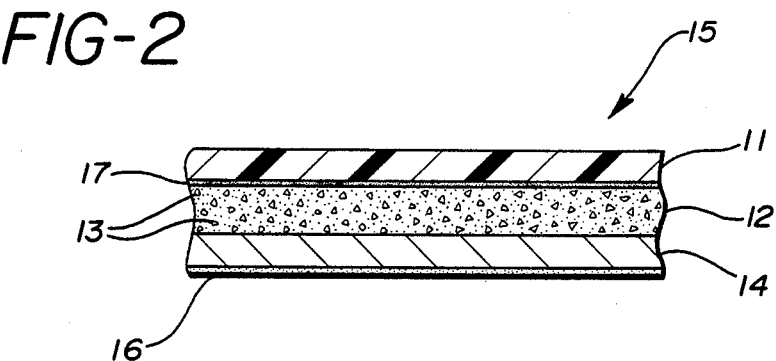
FIG. 2 is a fragmentary enlarged cross-sectional view depicting the system embodied in a preferred transdermal patch.

FIG. 2 depicts the preferred embodiment of a patch or bandage 15 which includes a facing adhesive 16 which is employed to affix the patch on the patient and also shows an adhesive layer 17 generally necessary to affix the drug reservoir member 12 to the backing member 11.

The drug reservoir is of a biologically acceptable silicone polymer matrix in which (+)-PHNO is dispersed and which matrix contains glycerol as cosolvent. By "dispersed", as herein employed, is meant that part of the drug is present as undissolved particles and part is dissolved in the matrix.

The biologically acceptable silicone matrix is of a silicone rubber which is capable of being cross-linked at either room temperature or elevated temperatures. A suitable silicone elastomer is one commercially available from Dow Corning Corporation, Midland, michigan as gDX-4-4210 Clean Grade Elastomer, having a durometer hardness of greater than about 25, shore A, points after 1 hour cure at 15° C. as measured by the ASTM or comparable test method. Other silicone elastomers having similar properties also may be employed.

The cosolvent to be employed in the transdermal system is glycerol. Other solvents such as PEG 400, propylene glycol, isopropyl myristate, isopropyl palmitate and the like were found not to provide the desired control or to have the desired compatibility with the drug and/or the silicone. The combined solvent system, i.e., the matrix silicone and the glycerol, partitions the (+)-PHNO in a manner to facilitate delivery of the drug.

It is contemplated in the transdermal delivery system to utilize a rate controlling membrane 14. A preferred membrane is a silicone elastomer which exhibits greater durometer hardness than the matrix elastomer. Suitable elastomers are such as those described in U.S. Pat. No. 4,162,243. One representative membrane is that made from Silastic ® Q7-4840 A/B medical Grade Liquid Silicone Rubber (Dow Corning Corporation, Midland, Mich.) which after curing has a durometer hardness, Shore A, of greater than about 40 points as measured by ASTM or comparable test method.

Generally speaking, the matrix polymer and membrane polymer are quite similar but with the membrane polymer exhibiting greater durometer hardness.

The backing 11 may be of any material in which the drug is impermeable. It may be of a vinyl acetate-vinyl chloride copolymer, polyethylene terephthalate, polyethylene, polyvinylidene chloride, polyester and other materials provided it has the properties of impermeability to the drug and strength and flexibility as a support. A preferred material is an aluminized polyester laminate such as that available as Scotchpak ® Film from 3M Company of St. Paul, Minn.

FIG. 2 depicts a preferred transdermal patch or bandage which in addition to the essentials of the transdermal system include parts for facile utilization and durability when applied to a patient. In the preferred patch, the membrane is provided with a pressure sensitive face adhesive 16. The facing adhesive serves to render the transdermal system a bandage or patch. The patch or bandage function may be supplied by a separate adhesive strip. However, a more useful patch with continuous contact is achieved by the use of a face adhesive. It is most desirable that the face adhesive be a silastic adhesive. The silastic adhesive will not only serve an adhesive function but will also have some rate controlling properties and co-act with the membrane in accomplishing the ultimate rate controlling results. Non-silicone adhesives are generally not suitable because the solubility and diffusibility of the drug in the non-silicone adhesives and/or the non-compatibility of the drug with the other components of the non-silicone adhesives adversely affect the controlled diffusion of the drug from the reservoir to the skin surface.

In addition, for a secure, durable patch, a thin adhesive layer 17 affixes the drug reservoir member 12 to the backing member 11. The use of an adhesive is desirable to assure secure attachment of the reservoir to the backing in view of the different nature of the matrix and backing polymers. Preferably, the adhesive selected should be one in which the drug is not very soluble.

The bandages or patches may be prepared by preparing laminated sheets of the necessary layers and thereafter die cutting to obtain the patches of the desired size.

Generally, the drug bearing matrix is prepared first by mixing together the drug, (+)-PHNO, and glycerol, milling both to reduce the size of the drug particles and to obtain a paste of the drug in glycerol, and then adding an appropriate amount of a mixture of elastomer pre-polymer and curing agent to the drug containing mixture. The mixture is passed through a roller mill to disperse the drug and to remove entrapped air, and then subjected to vacuum to deaerate and to obtain a reservoir matrix mixture.

There should be no drug particle greater than about 200 μm. The particles in general should be between about 5 μm and 50 μm although occasional particles greater than 50 μm do not have a detrimental effect.

The reservoir matrix mixture is then placed on a temporary backer sheet and faced on the opposite side with the rate-controlling membrane which is also on a temporary backer sheet, and the resulting matrix/membrane assembly is drawn through a pre-set gap of a gap coater and then transferred to an oven to cure the silicone elastomer of the matrix and to obtain a cured matrix/membrane assembly. The temporary backer sheet is conveniently a sheet of cellulose triacetate which subsequently may be discarded.

The curing may be carried out at room temperature or at elevated temperatures, depending on the prepolymer and curing agent or catalyst. Generally, elevated temperatures are employed and therefore the matrix sheet is heated in an oven. However, it may be placed in a temperature controlled box where there is no elevation of temperature.

The backing for the patch is prepared for attachment to the matrix/membrane assembly by coating with a solution of adhesive in a volatile solvent. After coating. the solvent is removed, generally by drying overnight at ambient temperature and thereafter at elevated temperatures. The backing may be protected on the adhesive side with a release liner until lamination to the drug matrix. The release liner is a removable liner, such as of wax paper or non-adhering sheet which serves to protect the adhesive and which may be removed and discarded.

After completion of the heating/drying processes, the backer sheet is stripped from the matrix/membrane assembly, and the release liner removed from the backing sheet and the backing laminated to the matrix/membrane assembly.

The laminated sheets constituting the essential components of the invention may be die cut to bandages of appropriate size.

The preferred patches are fitted with a face adhesive. For the preparation of these patches, the adhesive is applied to the laminated sheets prepared as above-described. The temporary backer sheet on the membrane on the face opposite that adhering to the matrix is removed and a pressure sensitive adhesive previously coated onto a release liner is transferred to the membrane. The resulting bandage assembly then may be die cut into individual patches.

The bandages are thin, being no greater than about 40g mils in thickness.

The reservoir may be from about 3 to 10 mils in thickness and is preferably about 7 mils. It may contain from about 1 to 5 percent by weight of (+)-PHNO, 0.5 to about 40 percent, preferably 5 to 10 percent of the cosolvent glycerol.

The membrane may be from about 1.5 to 15 mils in thickness. The preferred range is about 1.5 to 10 mils.

The thickness of the face adhesive is in the range of from about 1 to 5 mils, preferably 1 to 3 mils.

The thickness of the backing member is not critical except as it may affect flexibility and wearability. It is generally in the range of from about 3 to 5 mils.

The size of the patch depends in part on the amount of drug which must be delivered. Sizes suitable for providing therapeutic dose may be prepared in the range of from 2 to 30 square centimeters. The preferred range for most therapeutical uses is from about 10 to 30 square centimeters. The patch sizes have been found to be suitable for producing steady state plasma levels of (+)-PHNO of from about 100 to about 350g picograms per milliliter (pg/ml).

The optimum patch size for therapy of a given patient is based on the relationship $$\text{Steady State Concentration} = \frac{\text{net input rate}}{\text{total body clearance}}$$

where $$\text{net input rate} = \text{patch size} \times \text{net systemic flux}$$
$$= \text{patch size} \times \frac{1}{\frac{1}{\text{patch flux}} + \frac{1}{\text{skin flux}}}$$

The skin flux of (+)-PHNO has been determined to range from 1 mcg/cm$^2$/hr to 5 mcg/cm$^2$/hr in vitro.

The rate of release may be varied by varying the membrane thickness in accordance with the following relationship.

$$J = KCD/h$$

where
- $J$ = rate of release from patch ($\mu$g/cm$^2$/hr
- $K$ = partition coefficient between membrane and reservoir
- $D$ = diffusion coefficient of drug in membrane
- $h$ = membrane thickness Employing the patches of the present invention, therapeutic doses may be delivered at a rate of from about 2 micrograms to about 20 micrograms per square centimeter per hour.

The following examples illustrate the invention but are not to be construed as limiting

EXAMPLE I

The following operations were carried out to prepare 1000 patches of 5 cm$^2$ in size and containing 2.13 mg of (+)-PHNO per patch.

A dispersion of 2.13 grams of (+)-PHNO (free base) and 21.34 grams of glycerol was passed through a mill to reduce the particle size to that generally in the range of 5 to 50 $\mu$m.

83.2 grams of uncured elastomer (MDX4-4210 Clean Grade Silicone Elastomer from Dow Corning Corp.) consisting of 75.6 grams of silicone elastomer and 7.56 grams of curing agent was weighed into the drug/glycerol paste and the entire resulting dispersion was then passed through a three-roll mill to disperse the drug and minimize entrapment of air. The mixture then was deaerated under vacuum and portions of it dispensed between a cellulose triacetate backer sheet and a 1.5 mil polydimethylsiloxane rate-controlling membrane which was supported on the underside with another cellulose acetate backer sheet. The membrane/reservoir matrix assembly was hand-drawn through a pre-set gap of a gap coater and then transferred to a 70° C. oven for 1.5 hours to cure the silicone elastomer.

While the membrane/reservoir matrix assembly was being cured, a polyester film backing sheet was coated with a solution of silicone adhesive (B10-PSA® X7-2960) in an aliphatic petroleum naphtha solvent. After coating, the solvent was removed by drying at room temperature overnight.

The adhesive-coated impermeable backing was hand-laminated to the cured drug reservoir on the side opposite the rate-controlling membrane with the aid of a small rubber roller. Individual circular units, 5 square centimeters in size, suitable for patches were die-cut from the laminate sheets.

EXAMPLE II

A sheet of membrane/reservoir matrix assembly was prepared first in a manner similar to that described in Example I.

A face adhesive for the patch prepared as described in Example I was prepared by coating a solution of silicone adhesive (BIO-PSA g7-2960, Dow Corning Corp.) in aliphatic petroleum naphtha onto a release liner and the coated sheet dried for 4 hours at 70° C. to obtain a dry film coat with weight of 2.35 mg/cm$^2$.

The face adhesive thus prepared was laminated with the aid of a rubber roller to the membrane side of the membrane/matrix assembly Individual 4 square centimeter patches were then die cut from the laminated sheet.

EXAMPLE III

Patches were made in a manner similar to that described in Example I but in which the membrane thickness was varied. These patches had membrane thicknesses of 1.5 mils, 5 mils and 10 mils.

In vitro diffusion were then performed to determine the effect of membrane thickness on the release rate of (+)-PHNO from the transdermal patches.

Diffusion of (+)-PHNO through the membranes into isotonic 0.067M phosphate buffer medium at 32° C. in water-jacketed glass diffusion cells were determined by sampling the medium at various intervals and determining (+)-PHNO by fast HPLC. Separation was accomplished on a 5 cm C8 end-capped IBM column using a flow rate of 1.5 ml/gin and mobile phase of 50 percent acetonitrile in 0.01M pH g.0 phosphate buffer. Detection was by ultraviolet absorbance at 282 nm. The results seen in FIG. 3 show that J for 1.5 mil membrane was 18.6 $\mu$g/cm$^2$/hr; for 5 mil membrane, 8.2 $\mu$g/cm$^2$/hr; and for 10 mil membrane, 4.6 $\mu$g/cm$^2$/hr.

EXAMPLE IV

Patches having an adhesive facing were made in a manner similar to that described in Example II. The thickness of the membrane was 10 mils and the thickness of the face adhesive was 3 mils. The diffusion of the drug from the patches were determined as in Example III. The results seen in FIG. 4 show the rate controlling effect of the face adhesive on the release rate of the drug from the transdermal patches. The value of J for membrane without adhesive was 4.6 µg/cm$^2$/hr and that for membrane plus adhesive facing was 2.6 µg/cm$^2$/hr.

What is claimed is:

1. A therapeutic system in the form of a transdermal patch for administering (+)-PHNO comprising (a) a backing member impermeable to (+)-PHNO, (b) a reservoir of solid silicone polymer matrix containing (+)-PHNO and glycerol wherein the said solid reservoir matrix constitutes a solvent for the drug wherein in said matrix the drug is present in excess of its solubility and there is additionally present glycerol as cosolvent in an amount of from about 0.5 to no greater than 40 percent by weight, (c) a rate controlling membrane of silicone polymer, and (d) optionally a face adhesive and wherein said patch provides said (+)-PHNO at a therapeutic rate of from about 2 micrograms to about 20 micrograms per square centimeter per hour.

2. A method for delivering a therapeutic dose of (+)-PHNO sufficient to produce steady state plasma levels of (+)-PHNO of from about 100 to about 350 picograms per milliliter comprising employing the patch of claim 1.

* * * * *